United States Patent [19]

Boeckel et al.

[11] 4,314,523
[45] Feb. 9, 1982

[54] CENTRIFUGE ROTOR APPARATUS FOR PREPARING PARTICLE SPREADS

[75] Inventors: John W. Boeckel, Hamden; Vernon C. Rohde, Newtown, both of Conn.; John R. Wells, Culver City, Calif.

[73] Assignee: E. I. Du Pont de Nemours and Company, Wilmington, Del.

[21] Appl. No.: 131,678

[22] Filed: Mar. 19, 1980

[51] Int. Cl.$^3$ ............................................. B05C 13/00
[52] U.S. Cl. ...................................... 118/50; 118/52; 118/412; 233/13
[58] Field of Search .................. 233/13, 26, 27, 28, 233/34, 38, 45, 46; 118/52, 407, 50, 412; 427/2, 240

[56] References Cited

U.S. PATENT DOCUMENTS 3,672,564  6/1972  Schlutz ................................. 233/26
3,791,342  2/1974  Boyer ................................... 118/52

Primary Examiner—Robert W. Jenkins

[57] ABSTRACT

A centrifuge rotor is described which facilitates the preparation of cell dispersions on microscope slides. The rotor is bowl-like in configuration and defines plural peripheral regions adapted to receive the slides and a removable sample chamber associated with each slide. Each chamber has an outlet adpated to contact its slide. A sample, containing blood cells, for example, may be placed in a chamber and the cells centrifugally sedimented against the slide associated therewith. Excess or unwanted fluid is removed from the chamber by applying a vacuum through a vacuum line and hollow drive shaft. Leaf springs maintain each chamber in position and the vacuum line in fluid contact with the chamber. The vacuum line conecting each chamber cooperates with its leaf spring such that if a chamber is missing, the leaf spring closes the vacuum line.

9 Claims, 3 Drawing Figures

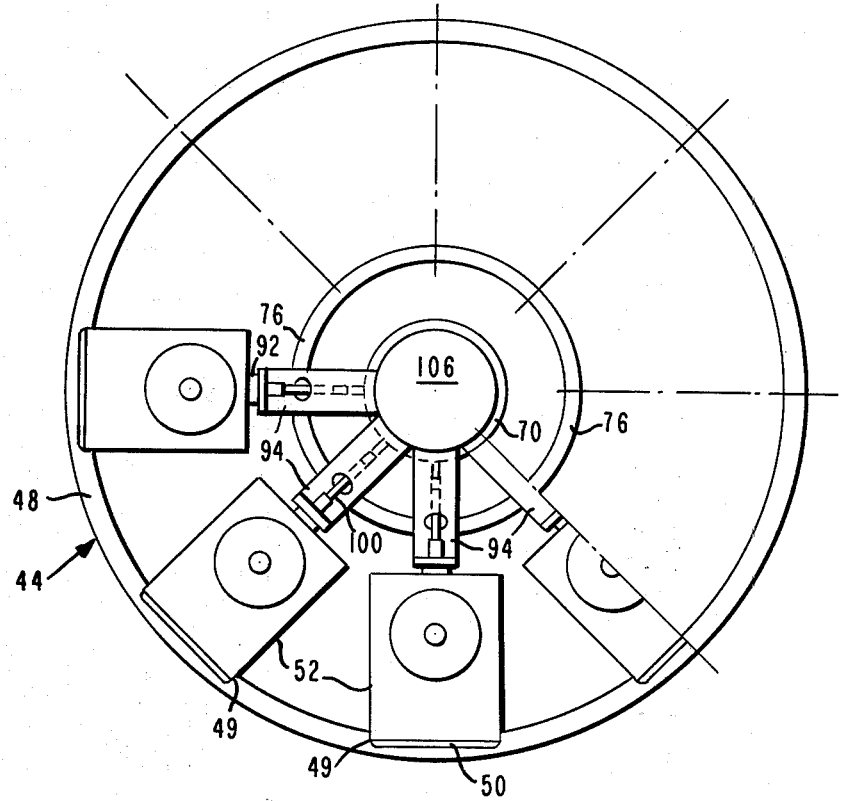
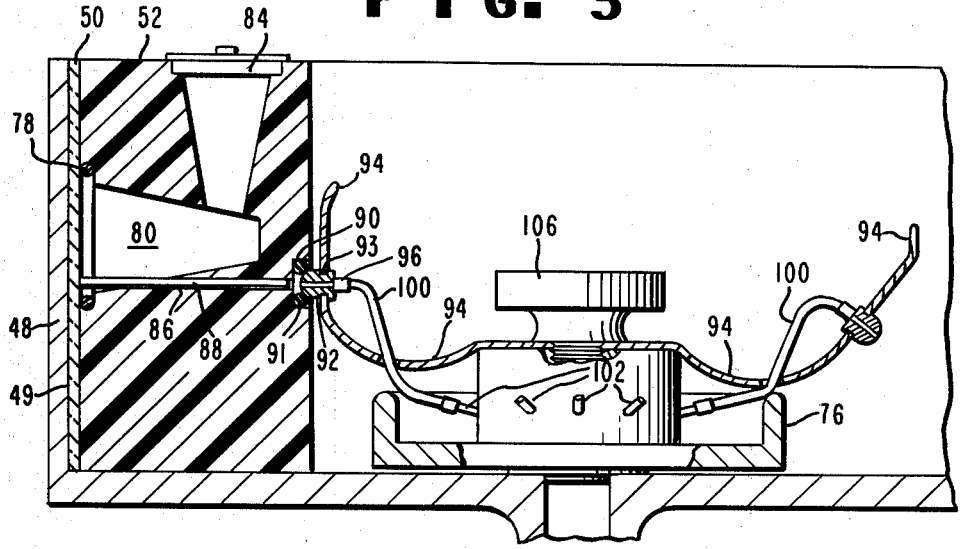

CENTRIFUGE ROTOR APPARATUS FOR PREPARING PARTICLE SPREADS

BACKGROUND OF THE INVENTION

Various devices are known for depositing blood cells on microscope slides. Among these are the devices described in U.S. Pat. Nos. 3,705,048 and 3,906,890. These devices rotate a slide about an axis perpendicular to the surface of the slide itself such that blood deposited on the slide is driven by centrifugal force across the surface of the slide, thereby widely distributing the blood cells of the sample. Such devices provide a relatively rapid, uniform technique for effecting blood counts and the like.

In other applications it is desirable to obtain a greater concentration of cells on the slide and to somewhat flatten the cells so that their structure may be more readily ascertained. One device for this purpose is available and sold under the name "Cytospin" by Shandon-Elliott. Such device utilizes a bowl-type centrifuge rotor whose outer periphery defines a vertical wall adapted to receive microscope slides. Chambers for holding samples to be sedimented are positioned radially against the slides with a piece of filter paper between each chamber and its slide. A hole in the filter paper is positioned over an outlet orifice of the chamber such that cells in a fluid introduced into the chamber, when centrifuged, are driven against the slide. The filter paper serves the function of withdrawing excess fluid from the surface of the slide such that the sedimented cells can remain in position following centrifugation.

Unfortunately, the filter paper can have a deleterious effect. It tends to absorb the fluid so rapidly that the cells are literally "sucked" or carried with the fluid into the peripheral edges of the filter paper surrounding the outlet orifice with relatively few cells having sufficient time to pellet or sediment against the slide itself. Also, the cells remaining on the slide tend to become dired since the filter paper absorbs most of the fluid. Generally, it is more desirable to sediment the cells while they are wet since they tend to remain rounded unless the applied centrifugal force exceeds the osmotic pressure of the cell. Another problem encountered with the use of filter paper is that the sample volume that can be used is relatively small. For this reason, usually only the cells of a single sample can be deposited on a given slide. The buildup of cells by the sedimentation of multiple sample on a single slide is difficult if not impossible to achieve.

A device similar to the Shandon-Elliott unit is described in an article entitled "A Device for Preparing Cell Spreads" by C. F. Dori et al., Immunology, 1965, 9, 403. Dori et al. note if the centrifugal force on the slides (and filter paper) is insufficient, a majority of the cells are pulled into the filter paper. Conversely, they note, too great a force or pressure prevents the preparations from drying in a short period of time (15 minutes). It is thus apparent that the devices of the prior art for preparing particle spreads on slides are somewhat critical and not entirely satisfactory.

A centrifuge rotor alleviating many of these difficulties is described and claimed in a copending application, Ser. No. 015,911, filed Feb. 28, 1979, by J. W. Boeckel et al. and assigned to the same assignee as the subject invention. In this rotor, conduit means communicate with each chamber for withdrawing excess fluid and are coupled to the rotor hub and thence through a fluid rotating seal to a suitable vacuum source. While quite satisfactory in general, this prior art device does encounter two disadvantages. One is that each vacuum line must be individually sealed off if it is not in use or else the vacuum may be decreased to a point which is undesirable. Secondly, since the fluid in the chambers are sucked generally upward, fluid sometimes becomes entrapped in cavities within the exhaust lines or conduits such that when a new slide is positioned for a run, some of the fluid from the preceding slide may fall back and contaminate the new slide.

SUMMARY OF THE INVENTION

According to the present invention, many of these prior art disadvantages are obviated by a centrifuge for depositing particles suspended in a sample disposed in a removable chamber on a deposition surface, the centrifuge comprising a bowl-like rotor having a radial inner wall defining circumferentially located regions, each adapted to receive one of the surfaces and one of said chambers in vertical disposition with each chamber being radially positionable in a circumferential region and having an outlet orifice for removably engaging its associated surface, thereby to hold a sample in contact with the surface, a hollow drive shaft for mounting the rotor, means for rotating the drive shaft, and tube means for removably interconnecting each said chamber with the hollow drive shaft for removing fluid from the chambers.

A vacuum source is connected to the drive shaft and the drive shaft is located below the rotor itself. A leaf spring is secured to the rotor for applying a radially outward spring bias to each chamber, thereby to maintain or to insure a leak-free contact between the chamber and the deposition surface. Further, a flexible conduit or tube is supported at one end by the spring means for fluid communication with a corresponding one in the chambers. The rotor is formed with an interior ringlike flange cooperating with the spring means such that, in the absence of a chamber, the spring means pinches the flexible tube. In a preferred form of the invention, the end of the tube in contact with the chamber is provided with a contact nozzle to maintain a fluid-tight connection to the chamber.

With this apparatus, excess fluid is removed from each chamber and withdrawn downwardly. Once removed it is virtually impossible for any fluid to pass back up into the chamber and contaminate a new slide during a subsequent run. Further if any chamber is not in position, the spring for maintaining that chamber in position, extends outwardly so as to close the vacuum line connected to that chamber. This insures that adequate vacuum is available to the chambers in use.

BRIEF DESCRIPTION OF THE DRAWINGS

Further advantages and features of this invention will become apparent upon consideration of the following description wherein:

FIG. 2 is an elevation view, partly in section, of the centrifuge drive assembly including the bowl-like rotor depicted in FIG. 1; and FIG. 3 is a fragmentary side elevation view of the rotor depicted in FIG. 1, illustrating in the one instance a single chamber in contact with the vacuum line and in another instance no chamber with the vacuum line at that position being pinched by the leaf spring.

DESCRIPTION OF THE PREFERRED EMBODIMENT

Figure 1:
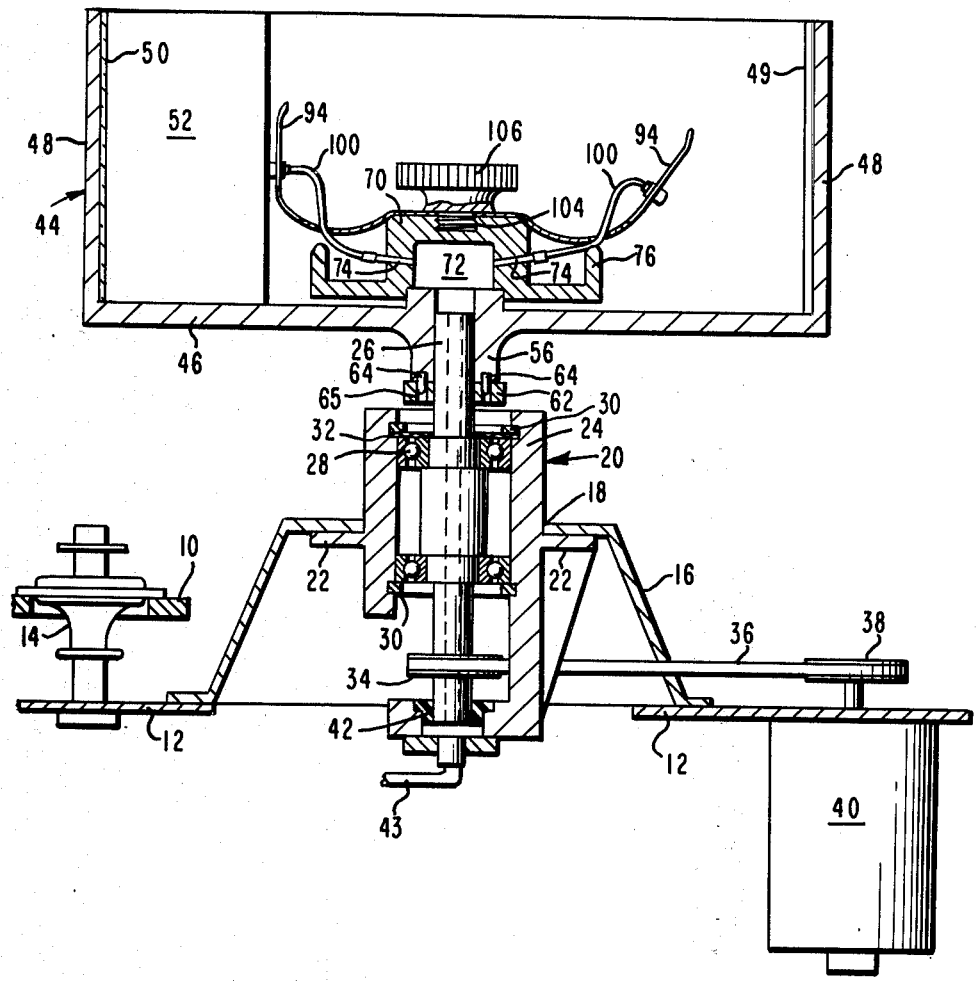
FIG. 1 is a partial plan view of a bowl-type centrifuge rotor constructed in accordance with this invention for depositing suspended particles on slides.

There may be seen in FIG. 1 a cross sectional illustration of a centrifuge constructed in accordance with this invention. The particular details of the housing for the centrifuge are not shown since they are not an inherent part of the invention. Any suitable housing, such as is typically used for a cell washer or small laboratory type centrifuge, may be used. In any event the centrifuge has a chassis 10 to which the rotor drive assembly and centrifuge rotor are secured. Thus a mounting plate 12 for the centrifuge drive assembly is resiliently secured to the chassis 10 as by a conventional vibration mount 14 formed of a resilient material. This serves to isolate the mounting plate from the chassis so that mechanical vibrations are not transmitted to the chassis. A mounting cone 16 may be secured, as by welding, to the mounting plate. The mounting cone 16 has a central opening 18 in which is secured a drive cartridge assembly 20. The drive cartridge assembly 20 has a flange 22 and is secured to the mounting cone as by welding the flange 22 to the underside of the cone adjacent the opening 18.

The drive cartridge assembly 20 includes an outer sleeve 24 in which is secured a hollow drive shaft 26. The drive shaft is mounted within the sleeve 24 as by bearings 28 which are secured in position by suitable C-rings 30 and a wavy washer 32. The exterior of the hollow shaft is suitably undercut to facilitate its mounting within the bearings and to prevent axial movement of the shaft. The lower portion of the shaft has a drive pulley 34 secured thereto and is driven by means of a belt which in turn is driven by the drive pulley 38 of a motor 40 which may be mounted to the mounting plate 12. The extreme lower end portion of the hollow drive shaft 26 is rotated within a stationary seal 42 to which is attached a suitable vacuum takeoff line 43 which is in turn coupled to a suitable vacuum source (not shown).

A rotor 44 is removably mounted on the top end of the drive shaft 26. This is accomplished by forming the rotor 44 to have a bowl-like configuration with a base 46 and side walls 48. The inner side walls 48 are formed with vertically oriented, peripherally spaced slots 49. The slots 49, as will be described, are adapted to accommodate a deposition surface 50, such as a microscope slide, and a sample holder 52 (see FIG. 3). The rotor thus far described is similar to that described in the Boeckel et al. application.

A hub 56 is formed in the central portion of the base 46 of the rotor and has two pins 64 mounted therein. The hub is placed over the upper end of the hollow drive shaft and rests upon a mounting collar 62 having holes 65 formed therein and located to engage the pins 64 to facilitate driving the rotor.

A collection cap or hub 70 is secured by a friction fit other suitable means, to afford a quick disconnect for cleaning, to the hub 56 on the base 46 of the rotor 44. The collection hub 70 cooperates with the hub 56 to provide a central vacuum cavity 72 which communicates with the hollow drive shaft 26. In this manner, vacuum may be applied through the drive shaft to the cavity 72. Orifices 74 are formed peripherally of the cavity 72 with a radial, slightly upward orientation in the wall of the collection hub. The lower portion of the collection hub is also formed to have an outer annular ring 76 for purposes as will be described in a moment.

As previously mentioned, the sample holders 52 are adapted to contact the slide or deposition surface 50 in a manner similar to that described in said copending Boeckel et al. application. For this purpose, an O-ring or similar device 78 is fitted in a recess in the radial outside surface of the sample holder to contact the microscope slide 50 and form a seal between the slide 50 and the sample holder. The sample chamber 80 itself is formed within the holder so as to permit the introduction of fluid samples through the upper wall of the chamber and is flared radially outwardly to minimize wall effects during centrifugation. A plug 84 may be used to close off the top of the chamber. Thus far described, the sample holder is substantially as described by Boeckel et al.

In accordance with this invention, a bore 86 (FIG. 3) is formed along the width (radial) dimension of the sample holder 52 and a tube or cannula 88 is slidably positioned therein. The contact end of the cannula may be slotted or sloped or otherwise shaped so as to permit the cannula to be used to withdraw fluid from the sample chamber 80. The angle of the slope determines how much fluid is withdrawn. Thus a large angle (a sharp pointed cannula) leaves a great amount of fluid while a small angle (a blunt point) withdraws most of the fluid. The length of the cannula 88 is selected to have one end in contact with the slide 50 and the other end extending to the region of a recess 90 formed in the back (radially inner) face of the sample holder 52. An O-ring seal 91 is positioned in the recess 90 such that it can be contacted by a nozzle 92 formed of a suitably resilient material. The nozzle 92 is formed with an annular slot 93 (such that it is in the nature of a grommet). The nozzle is adapted to be positioned within a hole formed in the end of a leaf spring 94 with the slot engaging the edges of the hole so that the nozzle is properly mounted on the leaf spring. The nozzle itself has a rear nipple 96. A flexible connecting means such as a tube 100, interconnects the nipple 96 with the nipples 102 which are force-fitted into the orifices 72 formed in the collection hub 70. Thus vacuum may be applied through the flexible tube 108 to the cannula 88 and thence to the sample chamber 80 itself to withdraw fluid from the immediate vicinity of the slide 50.

The top portion of the collection hub 70 has a bore 104 formed therein. The bore 104 is threaded to accommodate a clamping knob 106 which has a threaded stud adapted to engage the bore. The knob secures a spider-like spring stamping 108 which includes the individual leaf springs 94. The respective leaf springs 94 are positioned at the respective positions of each sample holder and slot 49. While a single stamping is illustrated, separate leaf springs may be used as well. The individual springs 94 are formed to flex into a general C-shape and apply sufficient pressure to maintain the sample holders 52 in position against the slides 50 (deposition surfaces) and the nozzles 92 pressed against the O-ring seals 91 to maintain a fluid tight seal as will be described.

In operation, each of the sample holders are positioned against a slide 50. Then, one at a time, each leaf spring 94 is withdrawn (compressed) by one's finger to permit the sample holder and slide combinations to be introduced into a slot 49 (chamber position). The leaf spring then is released. This allows the spring, acting through the nozzle 92, to press against the back face of the sample holder 52 and engage the seal 91.

Further in accordance with this invention moving the spring into a compressed position, as illustrated, in contact with the sample holder, opens the flexible tube 100. If no sample chamber is present, the spring presses the tubing 100 against the ringlike flange 76, thereby pinching the tube and preventing the vacuum from being applied through that tube. This reduces the load on any vacuum takeoff (43) and is an automatic means for accommodating different numbers of chambers.

When the rotor is spun, the vacuum may be applied to the respective sample chambers as desired from the vacuum takeoff 43 through the hollow drive shaft 26, the collection hub 70, the flexible tubes 100, nozzles 92, and cannulas 88 to the various sample chambers 80. Under centrifugal force, the cannulas 88 slide into contact with the microscope slide. This facilitates the accommodation of different manufacturing tolerances for the length of the cannula and insures adequate positioning of the cannula in most cases.

As is described in said copending Boeckel et al. application, typically the sample may be blood and blood cell suspensions which are to be deposited on the slide 50. For this application, the centrifuge is operated typically at several thousand revolutions per minute, although different speeds may be used depending on the results desired. Once the cells have become deposited on the slides, the vacuum is applied through the vacuum takeoff 43 so as to remove any supernatant (plasma in the case of blood) which is now virtually free of cells. The centrifuge may be continuously operated during this time due to the use of the seal 42 for the rotating hollow shaft 26. Following removal of the supernatant, the spinning operation may be continued to dry to slide if desired.

In any event, following cell deposition (and drying) the rotor may be stopped and the slide removed and examined, wet or dry. A particular advantage of this invention is that the supernatant is withdrawn downwardly through the fluid removal lines such as that there is little possibility that the supernatant from a preceding run can remain trapped in the vacuum line or tubes to contaminate a later centrifuge run. Any trapped fluid will fall by gravity away from the sample holders. All fluid lines are essentially down and located below the sample holders.

There has thus been described a relatively simple centrifuge capable of depositing particles on slides or the surfaces. The apparatus adequately positions the sample chambers, closes the vacuum line to any unused sample chambers positions and reduces the contamination between successive samples from the vacuum system.

We claim:

1. A centrifuge for depositing particles, suspended in a sample, on a deposition surface, said centrifuge comprising:
   a rotor having a wall defining plural circumferentially located regions each adapted to receive one of said surfaces, each of said regions adapted to removably receive a chamber having an outlet orifice for removably engaging one of said surfaces and adapted to hold said sample in contact with said one surface,
   a hollow drive shaft for mounting said rotor,
   means for rotating said drive shaft,
   a plurality of tube means each adapted to removably contact a different one of said chambers, thereby to interconnect said chambers with said hollow drive shaft for removing fluid from any said chamber in contact with said one surface.

2. The centrifuge of claim 1 which includes means communicating with said hollow drive shaft for applying a vacuum to the interior of said drive shaft.

3. The centrifuge of claims 1 or 2, which also includes
   a collection cap secured to the upper end of said hollow drive shaft to define a vacuum cavity,
   plural orifices in said cap,
   an outwardly extending leaf spring secured to said cap at each orifice position,
   a plurality of flexible tubes communicating at one end with a respective orifice and the other end being biased by a respective leaf spring radially outward, thereby to facilitate removable fluid communication with a chamber region.

4. A centrifuge of claim 3 wherein the other end of each said tube is provided with a nozzle for removable fluid contact with said chamber region.

5. A centrifuge of claim 4 wherein said cap includes a ring-like flange forming a pinch surface for closing each of said tubes by a respective one of said spring leafs when no chamber is present in a chamber region.

6. A centrifuge of claim 1 or 5 wherein each said region is defined by radially inward flanges for positioning a chamber and surface therein.

7. A centrifuge for depositing particles, suspended in a sample, on a deposition surface, said centrifuge comprising:
   a rotor having a wall defining plural circumferentially located regions each adapted to receive one of said surfaces, each of said regions adapted to removably receive a chamber having an outlet orifice for removably engaging one of said surfaces and adapted to hold said sample in contact with said one surface;
   a hollow drive shaft for mounting said rotor;
   means for rotating said drive shaft;
   a plurality of tube means each adapted to removably contact a different one of said chambers, thereby to interconnect said chambers with said hollow drive shaft for removing fluid from any said chamber in contact with said one surface;
   means communicable with said hollow drive shaft for applying a vacuum to the interior thereof; and
   means secured to said drive shaft for applying a radially outward bias to each said chamber, thereby to insure leak-free contact between each said chamber and a corresponding surface.

8. The centrifuge of claim 7 wherein each said tube means is flexible and is supported at one end by said spring means to facilitate fluid communication with a corresponding one of said chambers when a said chamber is positioned in one of said regions.

9. The centrifuge of claim 8 wherein said rotor is formed with an interior ring-like flange, said spring means operating, when not engaging one of said chambers, to pinch and close the flexible tube positioned at that chamber region.

* * * * *